United States Patent [19]

Blum

[11] Patent Number: 5,163,930
[45] Date of Patent: Nov. 17, 1992

[54] CONVEX INSERT FOR OSTOMY DEVICE

[75] Inventor: John L. Blum, South Toms River, N.J.

[73] Assignee: E.R. Squibb, Princeton, N.J.

[21] Appl. No.: 592,288

[22] Filed: Oct. 3, 1990

[51] Int. Cl.$^5$ .............................................. A61F 5/44
[52] U.S. Cl. .................................. 604/338; 604/342; 604/344; 604/355
[58] Field of Search ................ 604/327, 332, 335–339, 604/342, 355, 344

[56] References Cited

U.S. PATENT DOCUMENTS

| | | | |
|---|---|---|---|
| 4,781,708 | 11/1988 | Steer | 604/338 |
| 4,828,553 | 5/1989 | Nielsen | 604/339 |
| 4,889,534 | 12/1989 | Mohiuddin et al. | 604/339 |
| 5,004,464 | 4/1991 | Leise, Jr. | 604/344 |
| 5,088,992 | 2/1992 | Edwards et al. | 604/338 |

Primary Examiner—Randy C. Shay
Assistant Examiner—Gina M. Gueltieri
Attorney, Agent, or Firm—James & Franklin

[57] ABSTRACT

The insert is received within the coupling ring of the faceplate of a two piece ostomy device. The coupling ring has an axially extending rib and a rigid sealing flange defined in part by a radially inwardly extending surface. The insert includes a convex annular body with an arcuate relatively non-deformable portion and a deformable circumferential portion. The deformable portion has an outer edge with a circumference which is normally slightly larger than the inner circumference of the sealing flange. The circumference of the deformable portion is temporarily reduced as the insert passes through the ring. Once the insert is situated under the flange surface, the circumference returns to its normal dimension and the insert is securely seated.

20 Claims, 6 Drawing Sheets

CONVEX INSERT FOR OSTOMY DEVICE

The present invention relates to ostomy appliances and more particularly to an insert designed for use with the adhesive faceplate of a two piece type ostomy device to provide it with a convex curvature.

Various types of surgical procedures, such as colostomies, ileostomies and urostomies result in an opening or stoma in the abdominal area through which the body discharges waste. Since the patient has no control over the waste discharge, it is necessary to provide an appliance which both protects the stoma and acts as a collection receptacle for waste as it is discharged.

Different types of ostomy devices are known in the art. Many of these devices include a planar flexible faceplate or dressing with an adhesive surface designed to be affixed to the peristomal area on the skin of the patient. An opening in the faceplate aligns with and receives the stoma. A pouch or bag is sealingly attached to the reverse side (pouch side) of the faceplate.

In one popular type, a two piece construction is utilized wherein the pouch is removably mounted to the faceplate. U.S. Pat. No. 4,460,363 issued Jul. 17, 1984 to Steer et. al., entitled "Ostomy Bag", discloses such a two piece ostomy construction which has been very commercially successful. That patent teaches an ostomy pouch which employs a coupling system which includes a first coupling member, in the form of a plastic ring, which surrounds the stoma receiving opening in the faceplate, and a second coupling member, in the form of an annular channel, bonded to the ostomy bag around the inlet opening. The ring on the faceplate includes an axially extending rib which is dimensioned to sealingly engage the opening in the channel of the ring which is affixed to the pouch.

The axially extending rib includes an inwardly extending sealing strip. The strip is designed to be deflected when the rib is received within the channel. It remains partially deflected when in the channel so as to exert a force on the interior surface of the outer wall of the channel to maintain the rib securely within the channel.

A slightly modified version of the Steer structure is disclosed in application Ser. No. 530,635 filed May 30, 1990, in the name of John Victor Edwards, Walter F. Leise, Jr, and John B. Cline, entitled "Ostomy Device with Improved Coupling System". In that version the walls of the channel are made thinner and hence more easily deflectable. The channel is also provided with an inwardly directed protrusion which cooperates with the edge of the sealing strip in a manner which improves the positive interengagement between the rings. In a second embodiment the relatively deflectable sealing strip taught by Steer is replaced by a rigid, substantially non-deflectable sealing flange. In particular, the sealing flange is defined by a first surface which extends radially inwardly from and generally perpendicular to the surface of the axially extending rib and an inclined surface which extends from the edge of the rib which is received in the channel to the edge of the radially extending surface, so as to form a sealing flange which has a substantially triangular cross-section.

When the muscle surrounding the stoma of a patient lacks rigidity, because of advanced age or stretching, when the stoma does not sufficiently protrude beyond the skin surface or when the skin adjacent the stoma has a depression, scar or crease, it has been found that the conventional planar faceplates of ostomy devices often do not adequately adhere to the peristomal skin to create the necessary fluid tight and weight supporting seal. However, when the faceplate is provided with a convex curvature, a better seal between the peristomal stoma skin and the faceplate results. Further, a normally non-protruding stoma will be caused to protrude further into the stoma receiving opening. Hence, in some patients, it is desirable to utilize a faceplate with a convex curvature.

It is, of course, possible to fabricate ostomy devices with adhesive faceplates which have a convex curvature. However, it is economically impractical to produce such a line of specialized ostomy devices, in the many different sizes required, for use by the relatively limited number of patients who require this specialized configuration. Accordingly, a simple plastic adapter or insert has been used in conjunction with conventional ostomy appliances having coupling rings with flexible sealing strips to cause a normally planar faceplate to have the required convex curvature. For example, see U.S. Pat. No. 4,219,023 to Galindo which relates to a convex insert for this purpose. ConvaTec, a division of E. R. Squibb & Sons Corporation of Princeton, N.J., a leader in the area of ostomy products, has commercially successfully sold a convex insert as well. When properly affixed to the pouch side of an adhesive faceplate, such an insert acts to improve contact between the adhesive and the peristomal skin area by providing the faceplate with a convex curvature.

With the ConvaTec insert, the center hole in the faceplate is enlarged to fit the stoma prior to placing the insert into the coupling ring on the pouch side of the adhesive faceplate. The insert has an annular configuration with a convex surface and is made of substantially rigid plastic. Different size inserts are provided having different circumferences which correspond to different size coupling rings.

While these convex inserts do result in a faceplate having the necessary convex configuration, they may occasionally tend to cause the pouch to accidentally detach from the faceplate. This is because the rim of the rigid insert is designed to lodge under the edge of the inwardly extending sealing strip situated on the axially extending rib and hence adjacent the rim of the inner wall of the pouch coupling ring when same is attached to the faceplate. The sealing strip is quite flexible due to the its rather thin cross-sectional configuration. The insert may exert sufficient force to cause the sealing strip to deflect to a degree where the force is applied to the rim of the pouch coupling ring in a direction away from the faceplate. This may cause the rib of the faceplate coupling ring to dislodge from the channel of the pouch coupling ring, causing accidental detachment of the pouch. Such accidental detachments are a result which is very undesirable, particularly because they unfortunately tend to occur when the pouch is full, due to the increased weight of the pouch.

The present invention relates to a convex insert of a unique construction which is designed for use with a coupling ring having an axially extending rib with an inwardly extending rigid sealing flange. The unique construction of the present insert permits the insert to deform as it is received within the coupling ring and thereafter return to its non-deformed state with the outer edge thereof securely lodged under the radially extending surface which partially defines the rigid sealing flange. The insert can not interfere with the interengagement between the coupling rings because it does not contact or exert any force on the pouch coupling ring.

It is, therefore, a prime object of the present invention to provide a convex insert for an ostomy device which cannot contribute to the accidental detachment of the coupling rings.

It is another object of the present invention to provide a convex insert for use with an ostomy device of the type which includes a coupling ring formed of an axially extending rib with an inwardly extending rigid sealing flange.

It is another object of the present invention to provide a convex insert for an ostomy device which is deformable to permit the insert to pass through the coupling ring on the faceplate and thereafter return to its non-deformed condition securely lodged under the rigid sealing flange of the coupling ring.

It is another object of the present invention to provide a convex insert for an ostomy device wherein the insert includes a convex annular body with a substantially non-deformable portion having an arcuate cross section and a deformable portion having an outer edge with a circumference which may be temporarily reduced to permit the insert to pass through the coupling ring sealing flange.

It is another object of the present invention to provide a convex insert for an ostomy device wherein the deformable portion of the insert body includes a plurality of spaced deflectable portions adapted to flex to decrease the circumference of the outer edge of the insert.

SUMMARY OF THE INVENTION

In accordance with one aspect of the present invention, an insert is provided for a faceplate of a two piece ostomy device of the type including a coupling ring having axially extending rib means. Rigid sealing flange means on the rib means are partially defined by a substantially radially inwardly extending surface. The flange means have a given inner circumference. The insert includes a substantially convex annular body. The body includes a relatively deformable portion. The deformable portion has an outer edge with a circumference which is normally slightly larger than the flange means inner circumference. The circumference of the outer edge of the deformable portion is adapted to be temporarily reduced to permit the insert to pass through the flange means of the coupling ring and thereafter return toward its undeformed state such that the outer edge lodges under the radially extending flange means surface.

The flange means is further defined by a surface extending inwardly from the edge of the rib to the edge of the radially extending surface at an incline with respect thereto. The inclined surface cooperates with the deformable portion to facilitate reduction of the circumference of the outer edge, as the insert is inserted through the coupling ring.

The deformable portion includes substantially deflectable means. Flexing of the deflectable means results in the reduction in the circumference of the outer edge.

The deflectable means comprises a plurality of spaced deflectable areas. The deflectable areas are spaced around the circumference of the deformable portion. Relatively non-deflectable areas are situated in between the deflectable areas. The deflectable areas are thinner than the non-deflectable areas.

The deformable portion is substantially non-arcuate. The insert further includes a non-deformable portion which is thicker than the deformable portion.

The rib means comprises a surface which forms a corner with the radially extending flange means surface. The outer edge lodges in the corner when the insert is properly seated.

In accordance with another aspect of the present invention, a combination is provided including a faceplate for a two piece ostomy device and an insert adapted for use therewith. The faceplate includes the coupling ring having axially extending rib means. Rigid sealing flange means is partially defined by a substantially radially inwardly extending surface. The flange means has a given inner circumference. The insert includes a substantially convex annular body. The body includes a relatively deformable portion. The deformable portion has an outer edge with a circumference normally slightly larger than the inner circumference of the flange means. The circumference of the outer edge of the deformable means is adapted to be temporarily reduced to permit the insert to pass through the coupling ring and thereafter to return towards its original condition such that the outer edge lodges under the flange means surface.

BRIEF DESCRIPTION OF THE DRAWINGS

To these and such other objects which may hereinafter appear, the present invention relates to convex insert for an ostomy device, as described in detail in the following specification and recited in the annexed claims, taken together with the accompanying drawings, wherein like numerals refer to like parts and in which:

DETAILED DESCRIPTION

Figure 1:
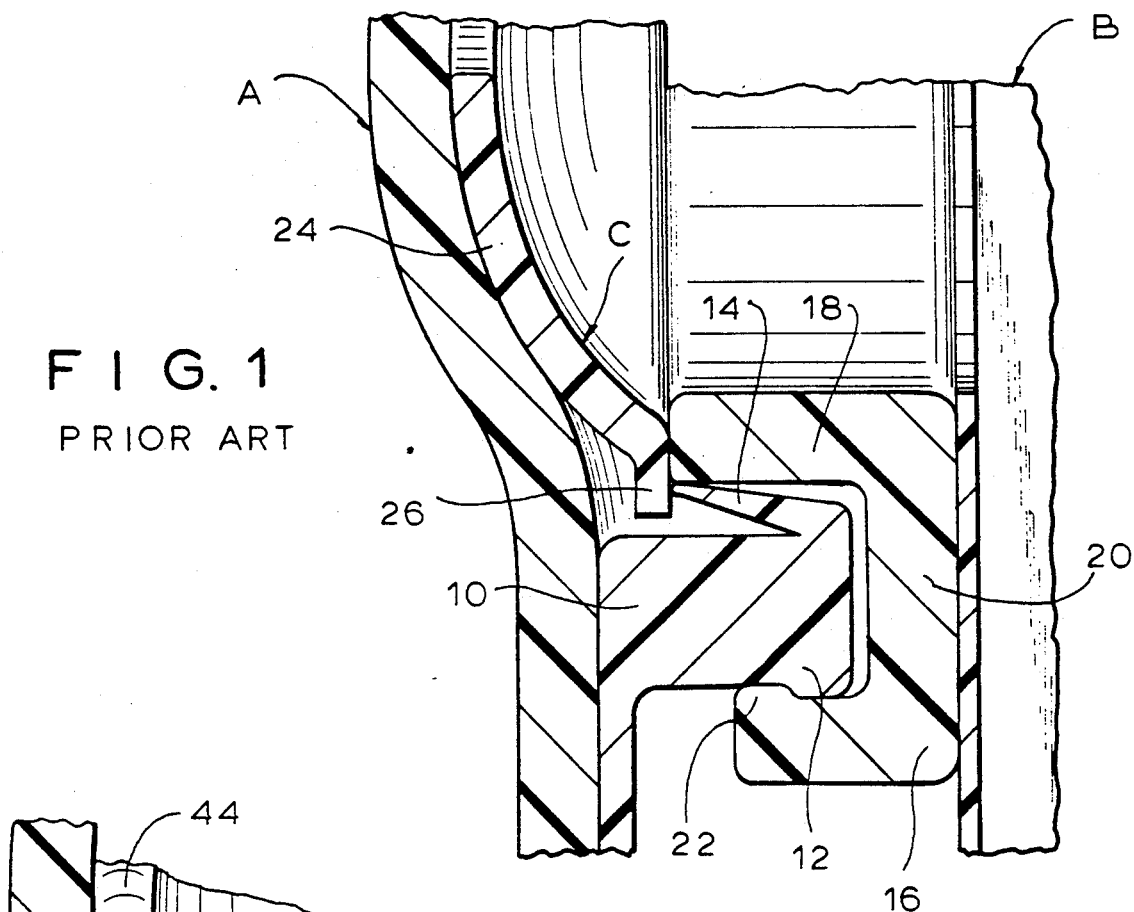
FIG. 1 is an enlarged cross-sectional view of a portion of a prior art two piece ostomy device with a conventional insert therein.

FIG. 1 illustrates a portion of an ostomy device with the Steer coupling system as disclosed in the above mentioned U.S. Pat. No. 4,460,363. That patent discloses an ostomy device which includes a flexible faceplate, generally designated A, which is normally substantially planar. Faceplate A includes a layer of medical grade adhesive adapted to be affixed to the peristomal surface of the skin, with a central opening therein aligned with the stoma.

Affixed to the pouch side of faceplate A, by welding or the like, is a coupling ring which includes substantially axially extending rib 10. Rib 10 has an exterior surface with a radially outwardly extending rim 12. Extending from the interior surface of rib 10, in a direction inclined with respect thereto by an acute angle, is deflectable sealing strip 14. Strip 14 deflects as rib 10 is inserted into the channel and remains in a partially deflected condition when rib 10 is within the channel.

The collection bag or pouch, generally designated B, also has a coupling ring affixed thereto. The coupling ring associated with pouch B is in the form of a channel which is formed by an exterior wall 16 and interior wall 18, both of which extend in spaced generally parallel relation from a base wall 20. Walls 16, 18 and 20 define a channel into which rib 10 is adapted to be received. Proximate the end of wall 16 is an inwardly extending protrusion 22. Protrusion 22 cooperates with rim 12 to maintain rib 10 within the channel in part because the partially deflected strip 14 exerts a force on rib 10 directed toward wall 16 maintaining rim 12 in the recess formed along the interior surface of wall 16 between protrusion 22 and wall 20.

Prior to mounting pouch B on faceplate A, a convex insert, generally designated C, can be inserted through the coupling ring affixed on the faceplate so as to give the faceplate a substantially convex configuration, as shown in FIG. 1. Insert C is of conventional design. It has a generally annular body 24 with an arcuate cross-section and a radially outwardly extending lip 26. Insert C is made of relatively rigid plastic such that it is substantially non-deformable.

When insert C is placed on faceplate A, lip 26 is situated underneath the tip of sealing strip 14 and is held in place by the sealing strip. When pouch B is mounted on faceplate A, as is shown in FIG. 1, the outer edge of wall 18 is in direct contact with lip 26. The rigid insert C must exert considerable force on faceplate A to cause the faceplate to maintain the convex shape. An equal and opposite force is directed away from faceplate A and thus towards pouch B. This force acts through lip 26. It is applied on the tip of the deflectable sealing strip 14 and the edge of wall 18 of the pouch coupling ring. It may cause sealing strip 14 to deform and the edge of wall 18 to move away from the faceplate.

Thus, the presence of insert C may tend to cause the pouch coupling ring to move away from the faceplate coupling ring and the coupling rings may become detached. Such accidental detachment of the coupling rings is a severe disadvantage and often occurs when the pouch is full due to the additional weight thereof. This problem is completely eliminated by the present invention. In addition, the insert of the present invention also provides the faceplate A with a greater convex curvature than the conventional insert C.

Figure 4:
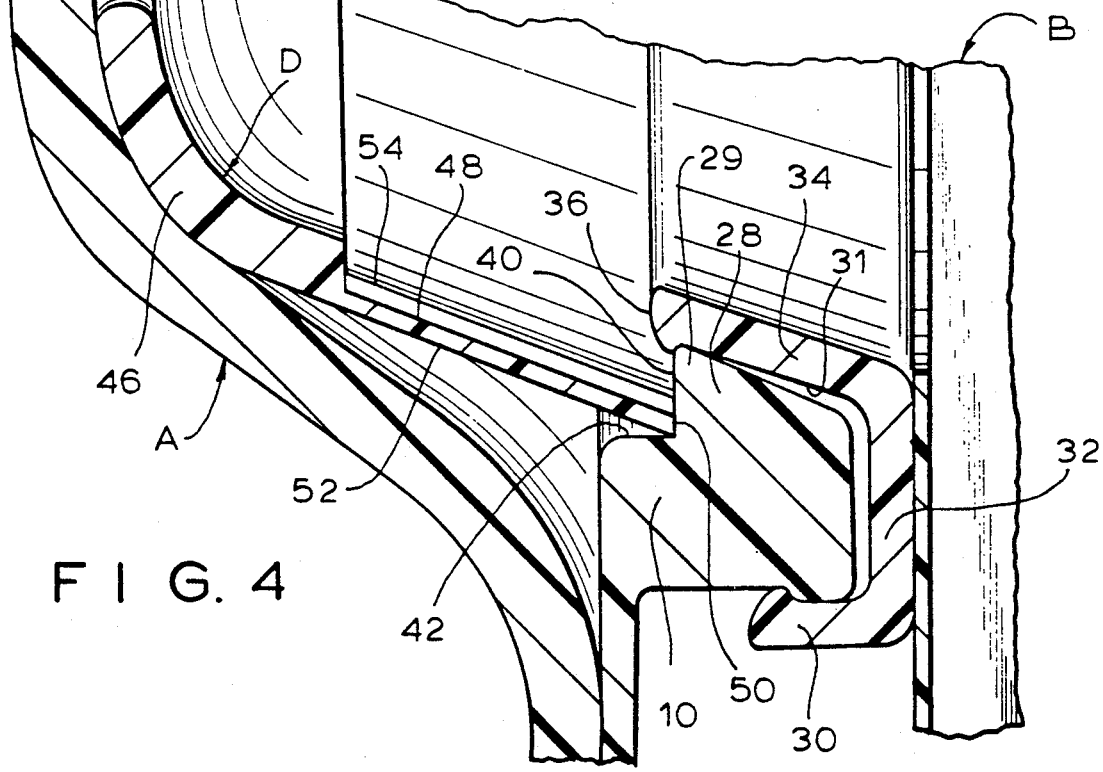
FIG. 4 is an enlarged cross-sectional view of a portion of the ostomy device illustrated in FIGS. 2 and 3.
Figure 2:
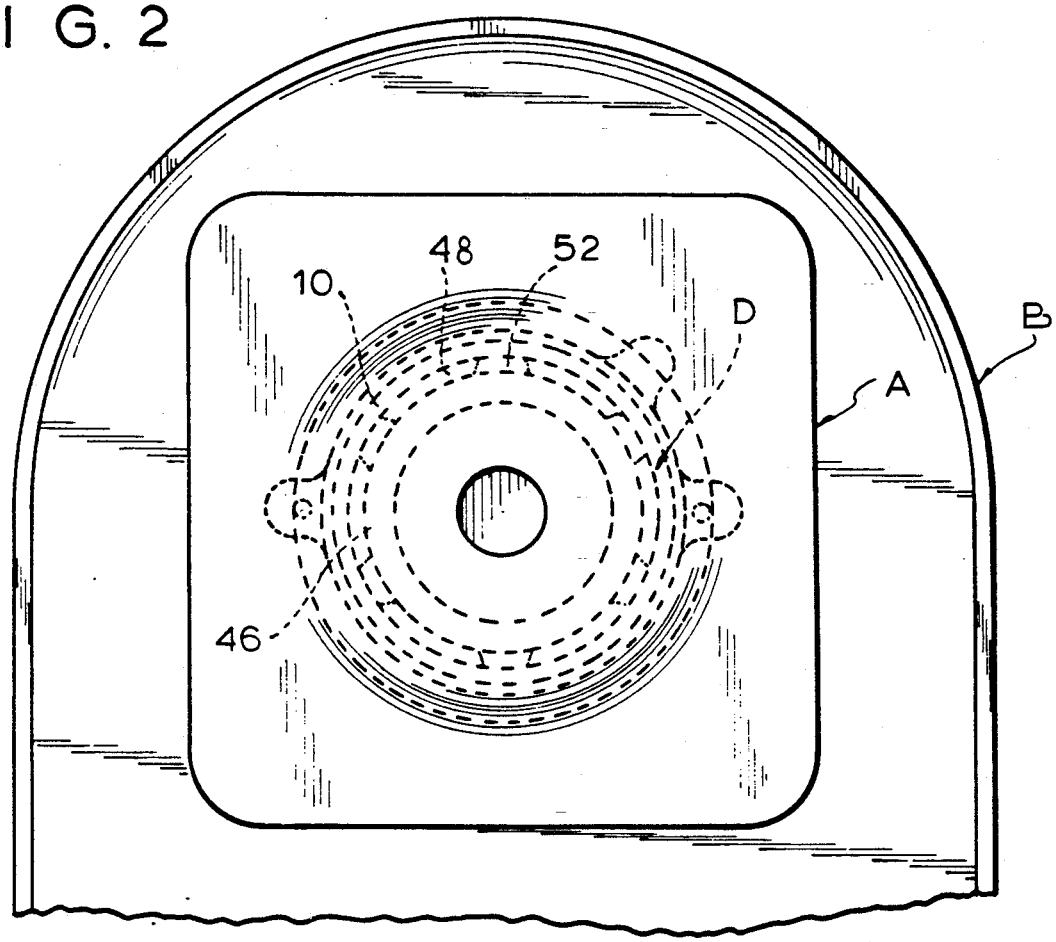
FIG. 2 is a elevational view of a portion of an ostomy device with the insert of the present invention mounted therein.
Figure 3:
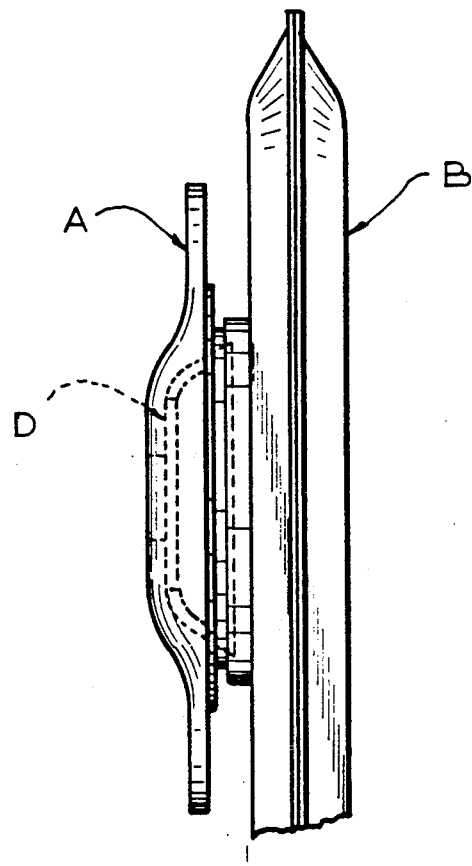
FIG. 3 is a side view of the ostomy device shown in FIG. 2.

FIGS. 2, 3 and 4 illustrate an ostomy device with the insert of the present invention, generally designated D, properly seated on the faceplate. In this case, the coupling rings of the ostomy device are modified as explained above and disclosed in the above mentioned application Ser. No. 530,635. That application describes the modified coupling ring structure in detail and the reader is referred thereto for additional information concerning same.

However, for purposes of this application, it is sufficient to understand that in the improved version of the coupling rings, the structure of rib 10 of the coupling ring affixed to faceplate A is modified to by eliminating the sealing strip 14, which is highly deflectable in the conventional version, and substituting a sealing flange 28 of solid plastic material which is rigid and hence substantially non-deflectable. The walls of 30, 32 and 34 which define the channel of the pouch coupling ring have been made substantially thinner and hence more deflectable as compared to the conventional channel. Moreover, the interior surface of inner channel wall 34 has been provided with an inwardly directed protrusion 36 designed to cooperate with the inner most edge 29 of sealing flange 28. With this modified configuration, the coupling force required to attach the coupling rings is reduced approximately 50% as compared to conventional configuration. At the same time, the detaching force is substantially increased to as much as at least twice that of the conventional device.

The insert D of the present invention cooperates with rib 10 but contacts same at a different location than the conventional insert C. In particular, as best seen in FIG. 4, the outer edge 50 of insert D, when the insert is properly seated, is lodged under the coupling ring on faceplate A, specifically adjacent the substantially radially extending surface 40 which extends inwardly from the rib toward the center of the coupling ring and in particular in the corner formed between surface 40 and the inwardly facing surface 42 of rib 10. When properly seated, the outer edge 50 of insert D is spaced from all parts of the pouch coupling ring and in particular from wall 34 thereof. Accordingly, no matter how much force is exerted by insert D, that force cannot be transferred to the pouch coupling ring to cause accidental decoupling of the coupling rings.

Figure 5:
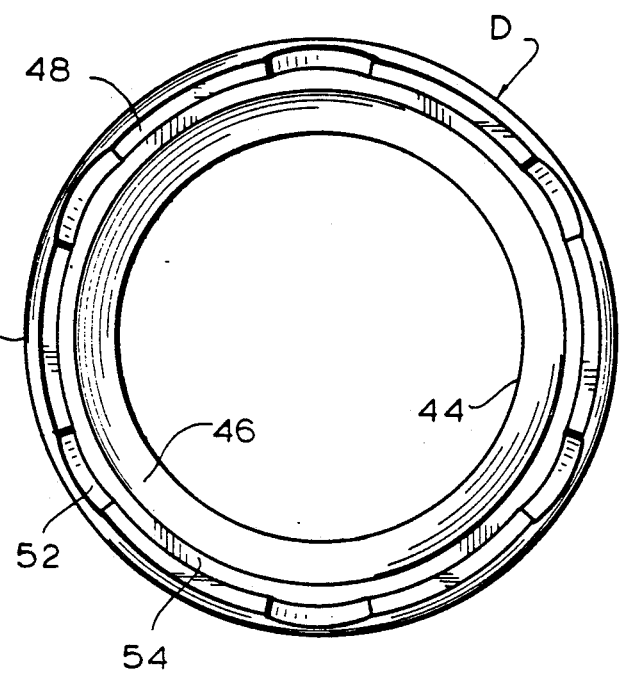
FIG. 5 is a plan view of the insert of the present invention.
Figure 6:
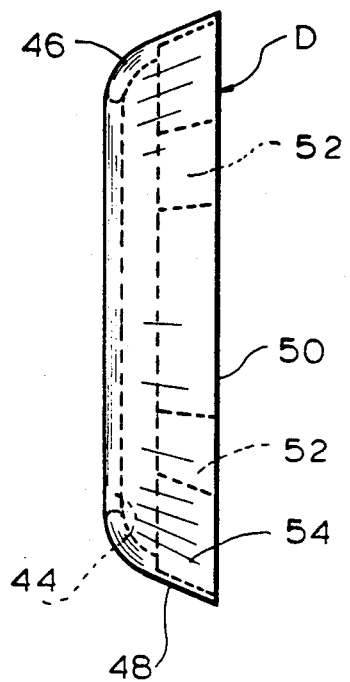
FIG. 6 is a side view of the insert of the present invention.
Figure 7:
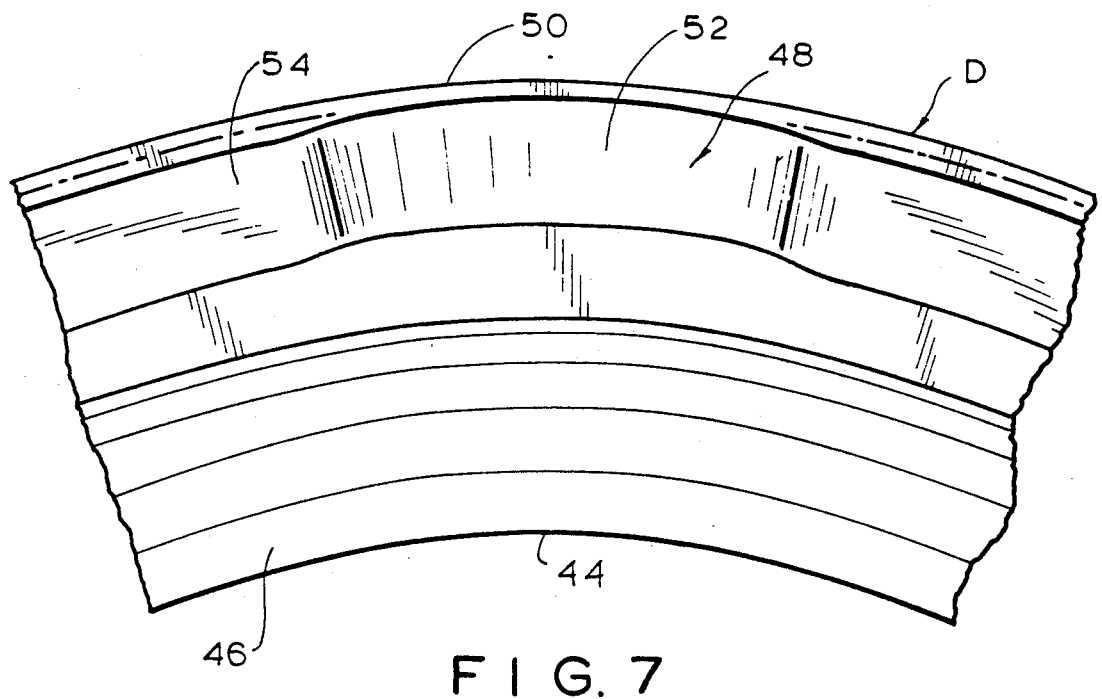
FIG. 7 is an enlarged view of a portion of the ostomy device of the present invention.
Figure 8:
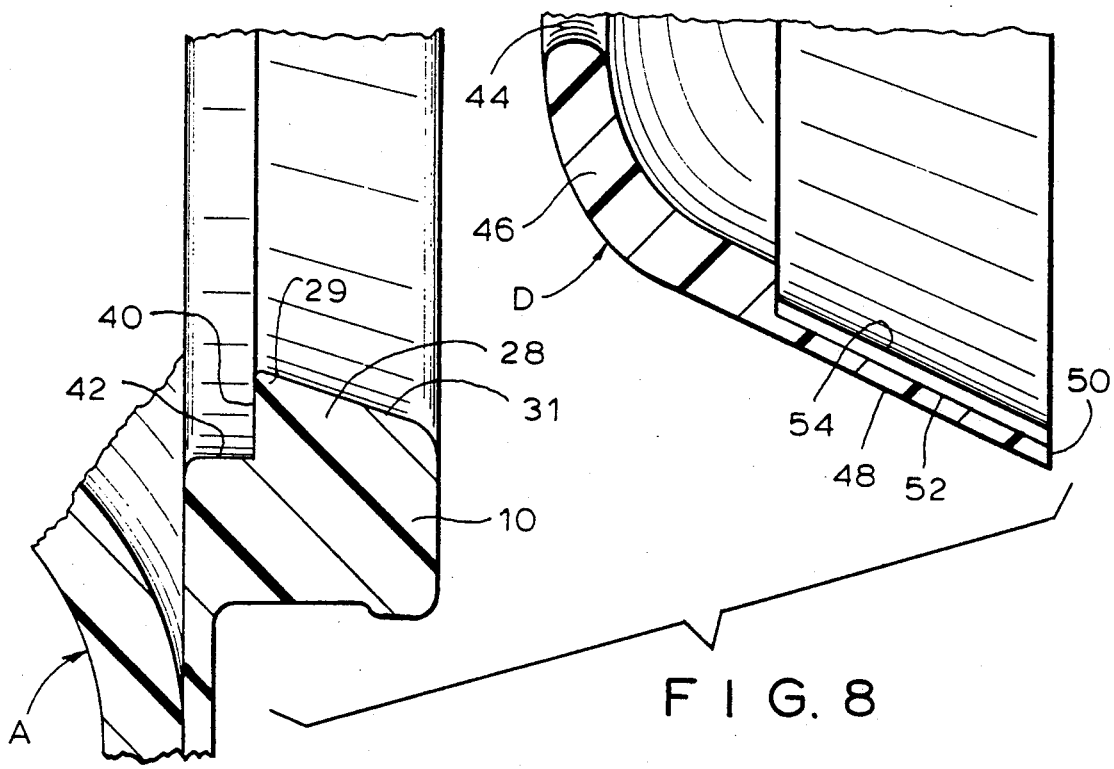
FIG. 8 is an exploded enlarged cross-sectional view showing a portion of the insert and coupling ring before the insert is received in the coupling ring.

The unique structure of the insert D is best appreciated with reference to FIGS. 5, 6 and 7. As can be clearly seen in these figures, insert D is substantially annular in configuration and has a central opening 44 designed to align the stomal opening in faceplate A. Insert D includes a substantially non-deformable base portion 46 which has a convex cross-section and which defines opening 44. Portion 46 is formed of plastic which is relatively rigid because of its thickness. Specifically, a thickness of approximately 0.06 inches is preferred.

Situated on non-deformable portion 46 is a relatively deformable circumferential portion 48 which has a substantially planar cross-section and an outer edge 50. Outer edge 50 has a circumference which, when portion 48 is in the non-deformed state, is slightly larger than the inner circumference of rib 10, as measured along the inner edge 29 of sealing flange 28. However, portion 48 is designed to deform, as insert D is mounted on faceplate A, such that the circumference of outer edge 50 is reduced temporarily to permit the insert to pass through the faceplate coupling ring. Once the insert has passed through the faceplate coupling ring, such that the outer edge 50 passes beneath inner edge 29 of the flange 28, the deformable portion 48 of insert D will return toward its non-deformed state, such that outer edge 50 lodges under surface 40 of flange 28 and in particular proximate the corner formed between surfaces 40 and 42, as shown in FIG. 4. The deformation of section 48 and the subsequent return of same towards its original circumference is possible because of the unique structure of the deformable portion 48.

Figure 9:
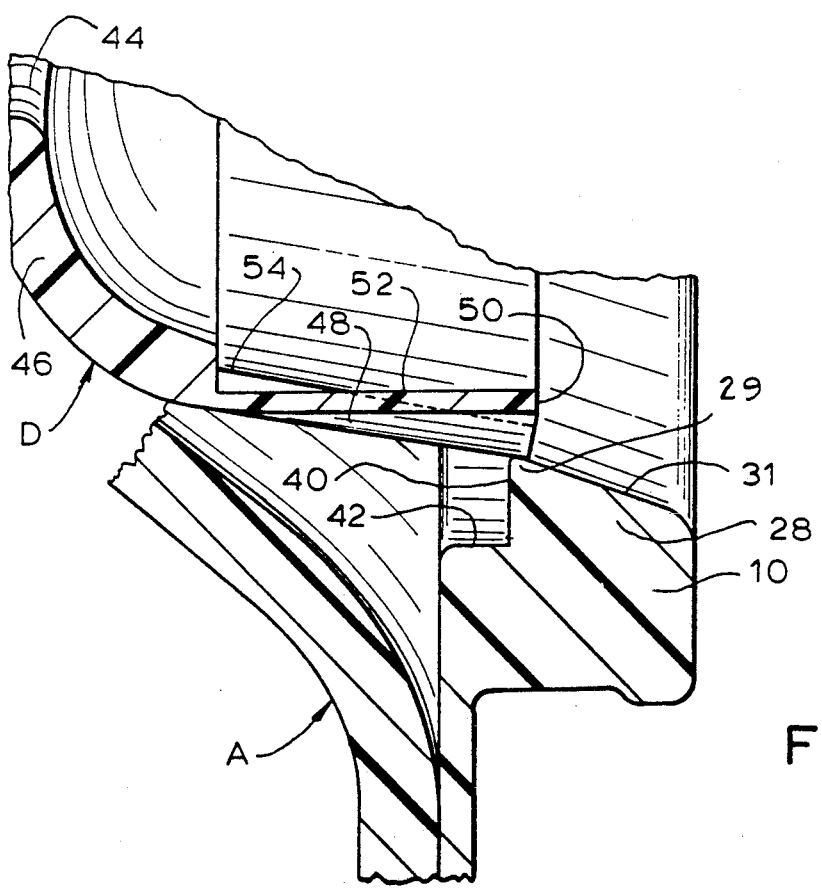
FIG. 9 is a view similar to FIG. 8 but showing the insert as it is being received within the coupling ring.
Figure 10:
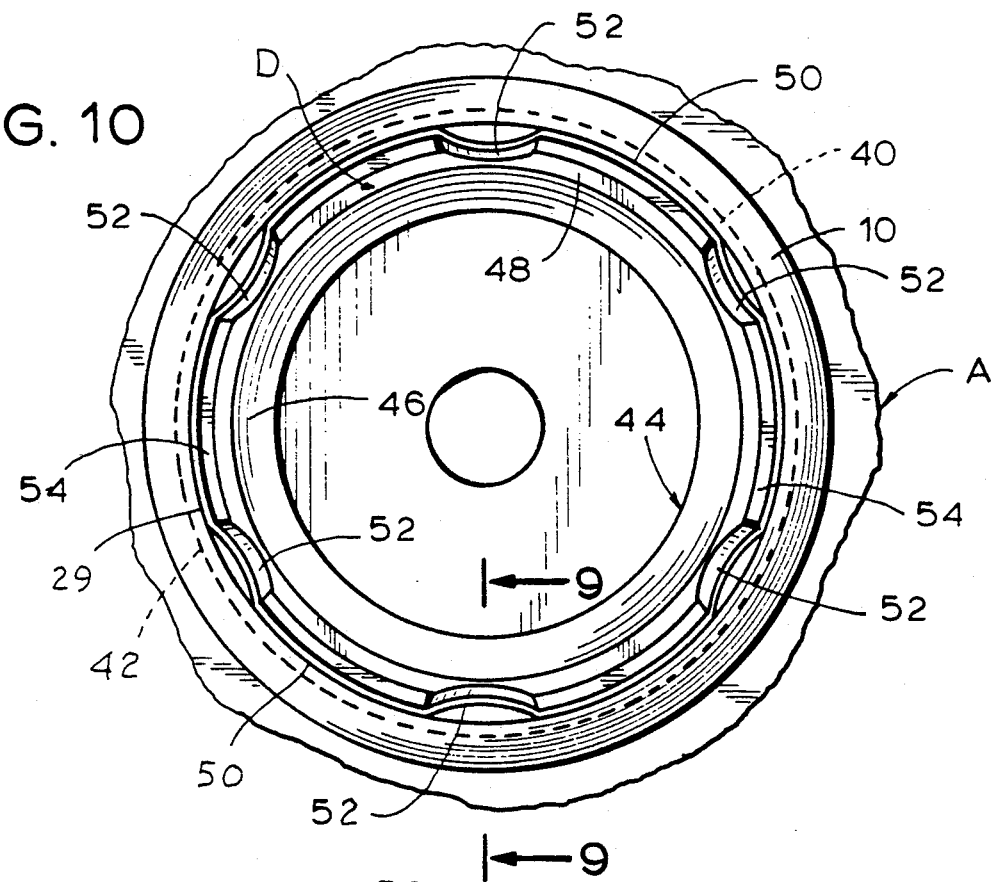
FIG. 10 is a plan view of the faceplate showing the insert in the condition illustrated in FIG. 9.

As seen in FIGS. 5 and 7, the deformable portion 48 of insert D is provided with a plurality of alternating thinner areas 52 and thicker areas 54. FIGS. 9 and 10 show the insert D as it is being mounted on a faceplate A and more particularly as the insert is passing through the faceplate coupling ring defined by rib 10. Because the inner circumference of rib 10 of the faceplate coupling ring, as defined at inner edge 29, is slightly smaller than the circumference of the outer edge 50 of insert D, in its non-deformed state, the circumference of outer edge 50 must be reduced in order to permit the insert to pass through the coupling ring. This is achieved by causing the thinner areas 52 of deformable portion 48 to flex inwardly, thereby decreasing the circumference of the insert. This occurs as the exterior surface of portion 48 proximate outer edge 50 is cammed over inclined surface 31 which extends from the leading corner of rib 10 to inner edge 29. Areas 52 are formed of sufficiently thin plastic material such that they have greatly increased flexibility, as compared with areas 54. In particular, it is preferable that the thicker areas 54 have a thickness of approximately 0.02 inch, as compared to that of the thinner areas 52 which are approximately 0.01 inch in thickness. Accordingly, areas 54 are preferably twice as thick as areas 52, permitting areas 52 to flex inwardly to substantially reduce the circumference of outer edge 50 and thereafter return to their normal position.

Figure 11:
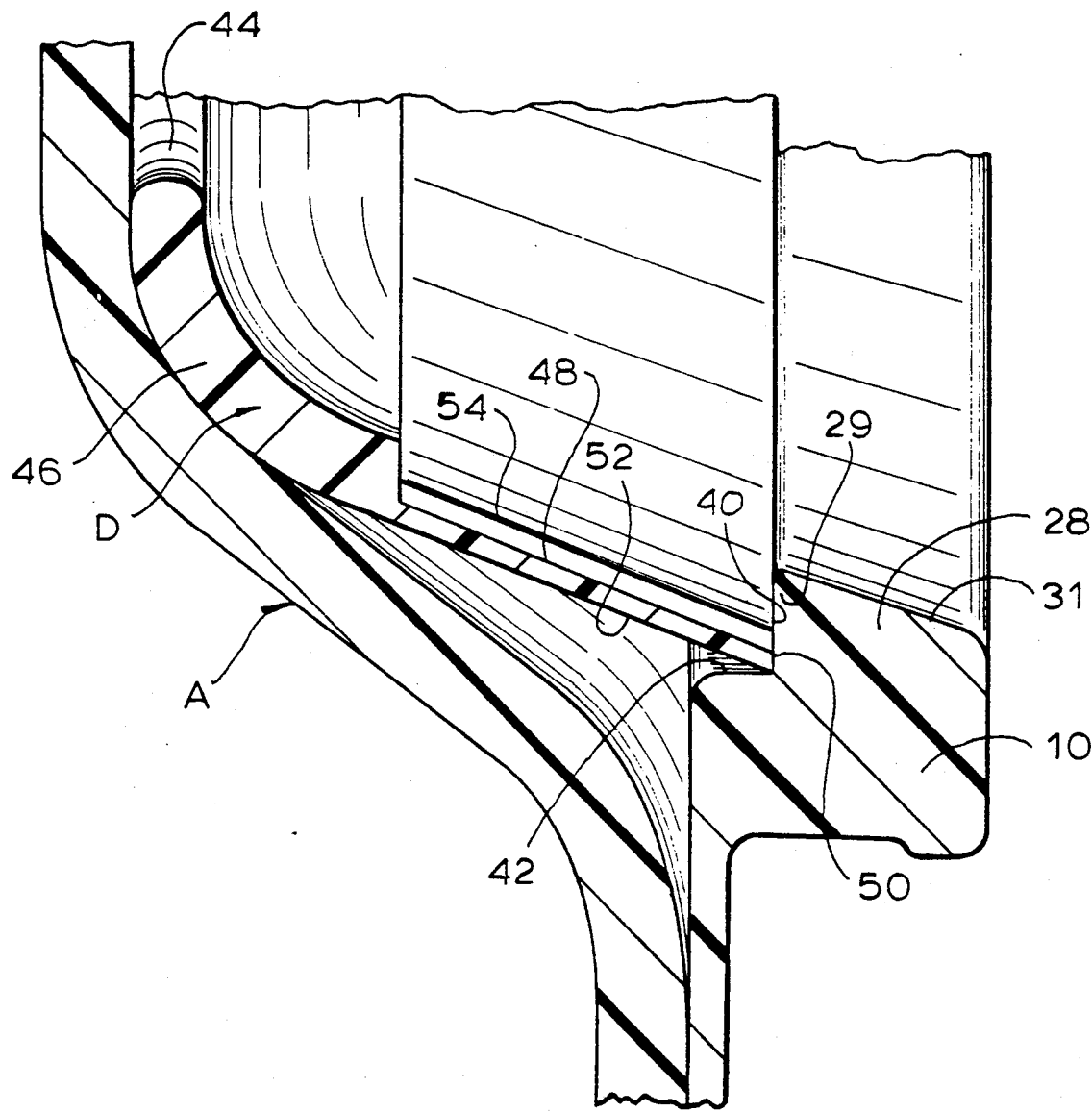
FIG. 11 is a view similar to FIG. 9 but showing the insert fully received within the coupling ring.
Figure 12:
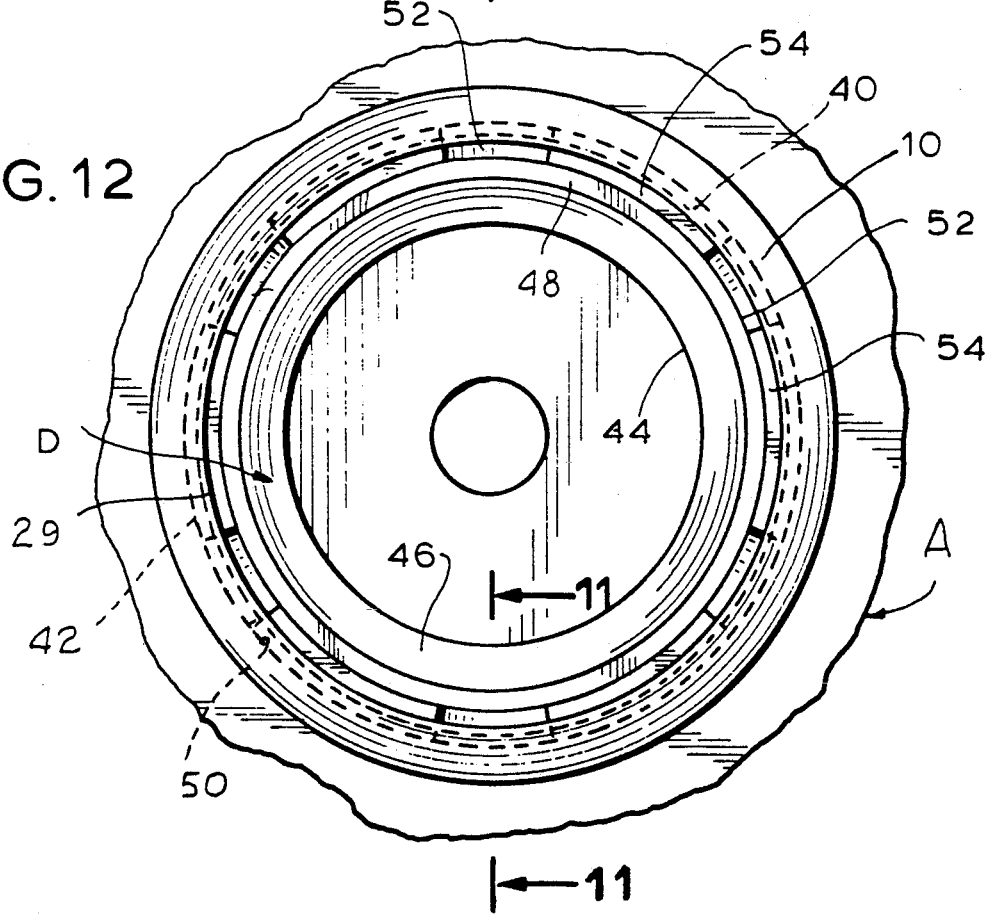
FIG. 12 is a plan view of a faceplate with the insert of the present invention received therein.

As illustrated in FIGS. 11 and 12, once insert D has passed over inner edge 29 of the sealing flange 28, it expands towards its original condition, thinner areas 52 returning to their original state, such that the insert is properly seated, being lodged under surface 40 and preferably with outer edge 50 within the corner formed by surfaces 40 and 42 of rib 10. Since the depth of insert D measured axially is greater than the depth of conventional insert C, when it is seated in place faceplate A will tend to have a greater convex curvature with the insert of the present invention than when the conventional insert is utilized.

Once properly seated under flange 28, it is difficult to remove the insert from the faceplate and accidental dislodgement of insert is virtually impossible. Moreover, since the insert does not contact or exert any force on the pouch coupling ring, it can not tend to detach the coupling rings.

It should now be appreciated that the present invention relates to an insert for use with the faceplate of an ostomy device to give a normally planar flexible faceplate a substantially convex configuration. The insert has a unique structure which includes a non-deformable annular base portion with an arcuate cross-section upon which is mounted a deformable circumferential portion comprising alternating thicker and thinner areas. The circumference of the outer edge of the deformable portion is normally slightly larger than the circumference of the inner edge of the faceplate coupling ring, such that when the insert is received on the faceplate and passes through the coupling ring, the deformable portion deforms slightly, such that the circumference of the outer edge thereof is sufficiently reduced to permit the insert to pass through the coupling ring. Once it has passed through the coupling ring, the deformable portion of the insert returns towards its original non-deformed state, such that the circumference of the outer edge thereof is again slightly larger than the inner circumference of the faceplate coupling ring, with the outer edge lodged underneath the coupling ring at a point thereon spaced from the pouch coupling ring. It therefore cannot apply any force on or in any way interfere with the pouch coupling ring, when the pouch is mounted to the faceplate.

While only a single preferred embodiment of the present invention is disclosed herein for purposes of illustration, it is obvious that many variations and modifications could be made thereto. It is intended to cover all these variations and modifications which fall within the scope of the present invention as define by the following claims.

I claim:

1. An insert for a faceplate of a two piece ostomy device, the faceplate having a surface and comprising a coupling ring affixed to the surface of the faceplate and having axially extending rib means with substantially rigid sealing flange means partially defined by a substantially radially inwardly extending surface, said flange means having a given inner circumference, said insert comprising a substantially annular body, said body comprising a non-deformable convex portion and a deformable portion, said deformable portion having an outer edge with a circumference normally slightly larger than said flange means inner circumference, said outer edge of said deformable portion being adapted to be temporarily reduced in size as said insert passes through said coupling ring to a position where said body is situated between the coupling ring and the faceplate surface and thereafter to return toward its original size such that said outer edge lodges under said flange means surface.

2. The insert of claim 1 where said flange means is further defined by a surface extending inwardly from the edge of said rib means to the edge of said radially extending surface, at an incline with respect to said radially extending surface, said inclined surface comprising means for cooperating with said deformable portion to facilitate reduction of the circumference of said outer edge, as said insert passes through said coupling ring.

3. The insert of claim 1 wherein said deformable portion comprises substantially deflectable means, deflection of said deflectable means resulting in said reduction in the circumference of said outer edge.

4. The insert of claim 3 wherein said deflectable means comprises a plurality of spaced deflectable areas.

5. The insert of claim 4 wherein said deflectable areas are spaced around the circumference of said deformable portion with relatively non-deflectable areas situated therebetween.

6. The insert of claim 5 wherein said deflectable parts are thinner than said non-deflectable areas.

7. The insert of claim 1 wherein said deformable portion is substantially non-arcuate when viewed in cross section.

8. The insert of claim 1 wherein said insert further comprises a non-deformable portion and wherein said non-deformable portion is thicker than said deformable portion.

9. The insert of claim 3 wherein said insert has an interior and wherein said deflectable means comprises means for flexing said deflectable means towards the interior of said insert.

10. The insert of claim 1 wherein said rib means comprises a surface which forms a corner with said flange surface and wherein said outer edge lodges in said corner when properly seated.

11. In combination, a faceplate of a two piece ostomy device said faceplate having a surface comprising a coupling ring affixed to the surface of the faceplate and having axially extending rib means and rigid sealing flange means partially defined by a substantially radially inwardly extending surface, said flange means having a given inner circumference, and an insert comprising a substantially annular body, said body comprising a non-deformable convex portion and a deformable portion, said deformable portion having an outer edge with a circumference normally slightly larger than said flange means inner circumference, said circumference of said outer edge being adapted to be temporarily reduced to in size permit said insert to pass through said flange means of said coupling ring to a position where said body is between the coupling and the faceplate surface and thereafter return towards its original size such that said outer edge lodges under said flange means surface.

12. The combination of claim 11 wherein said flange means is further defined by a surface extending inwardly from the edge of said rib means to the edge of said radially extending surface, at an incline with respect to said radially extending surface, said inclined surface comprising means for cooperating with said deformable portion to facilitate reduction of the circumference of said outer edge as said insert passes through said coupling ring.

13. The combination of claim 11 wherein said deformable portion comprises substantially deflectable means, deflection of said deflectable means resulting in said reduction in said circumference of said outer edge.

14. The combination of claim 13 wherein said deflectable means comprises a plurality of spaced deflectable areas.

15. The combination of claim 14 wherein said deflectable areas are spaced around the circumference of said deformable portion by relatively non-deflectable areas.

16. The combination of claim 15 wherein said deflectable areas are thinner than said non-deflectable areas.

17. The combination of claim 11 wherein said deformable portion is substantially non-arcuate when viewed in cross section.

18. The combination of claim 11 wherein said insert further comprises a non-deformable portion and wherein said non-deformable portion is thicker than said deformable portion.

19. The combination of claim 13 wherein said insert has an interior and wherein said deflectable means comprises means for flexing said deflectable means toward the interior of said insert.

20. The combination of claim 11 wherein said rib means comprises a surface which forms a corner with said flange surface and where said outer edge lodges in said corner when properly seated.

* * * * *